(12) United States Patent
Osawa et al.

(10) Patent No.: US 6,474,166 B1
(45) Date of Patent: Nov. 5, 2002

(54) METHOD FOR INDICATING CHARACTERISTICS OF ROTATING APPARATUS OR VIBRATING APPARATUS

(75) Inventors: Harushige Osawa, Kusatsu (JP); Tomohiro Hasegawa, Echi-gun (JP)

(73) Assignee: Nidec Corporation, Kyoto (JP)

( * ) Notice: Subject to any disclaimer, the term of this patent is extended or adjusted under 35 U.S.C. 154(b) by 107 days.

(21) Appl. No.: 09/610,150

(22) Filed: Jul. 5, 2000

(30) Foreign Application Priority Data

Jul. 5, 1999 (JP) .......................................... 11-190042

(51) Int. Cl.[7] .............................................. G01N 29/00
(52) U.S. Cl. ............................ 73/660; 73/579; 73/597; 73/593; 73/602; 73/1.37
(58) Field of Search ........................ 73/660, 659, 657, 73/649, 651, 579, 597, 598, 602, 1.37, 1.82, 593

(56) References Cited

U.S. PATENT DOCUMENTS

| | | | |
|---|---|---|---|
| 4,843,885 A | * 7/1989 | Bambara | ..................... 73/660 |
| 4,996,880 A | * 3/1991 | Leon et al. | ..................... 73/660 |
| 5,152,172 A | 10/1992 | Leon et al. | ..................... 73/579 |
| 5,541,857 A | 7/1996 | Walter et al. | ................. 73/660 |
| 5,720,248 A | 2/1998 | Crofts | ..................... 123/192.1 |
| 6,140,791 A | * 10/2000 | Zhang | ......................... 318/632 |
| 6,300,695 B1 | * 10/2001 | Neal | ......................... 310/68 D |
| 6,378,373 B1 | * 4/2002 | Metrikin | ..................... 73/593 |

OTHER PUBLICATIONS

Abstract of JP 05066150 w/Japanese laid–open application.
Abstract of JP 07128133 w/Japanese laid–open application.
Abstract of JP 09291315 w/Japanese laid–open application.

* cited by examiner

*Primary Examiner*—Daniel S. Larkin
*Assistant Examiner*—Jacques Saint-Surin
(74) *Attorney, Agent, or Firm*—Burns, Doane, Swecker & Mathis, LLP

(57) ABSTRACT

A method for visualizing and indicating characteristics of vibration measurement data for a rotating or vibrating object. Specific components are removed from the measurement data or are minimized therein. After removing or minimizing the specific component, the measurement data is indicated in a Campbell diagram.

5 Claims, 5 Drawing Sheets

METHOD FOR INDICATING CHARACTERISTICS OF ROTATING APPARATUS OR VIBRATING APPARATUS

This application claims priority under 35 U.S.C. §§119 and/or 365 to 11-190042 filed in JAPAN on Jul. 5, 1999; the entire content of which is hereby incorporated by reference.

BACKGROUND OF THE INVENTION

1. Field of the Invention

The present invention relates to an indicating method for visualizing and indicating measurement data, and particularly relates to a characteristics indicating method capable of visualizing the characteristics of a measured object from various types of measurement data measured for a rotating apparatus such as motors or turbines or the like, or non-rotating vibrating apparatus such as smokestacks or automobiles or the like, thereby enabling identification of the source of stimulus and estimation of the cause of abnormalities and vibrations.

2. Description of the Related Art

Spindle motors for rotating a disk-shaped recording medium are required to rotate at high speed, and at the same time, due to an increase of required data storage capacity, the motors are required to assume high precision of rotation, e.g. decrease vibration components asynchronous with the rotation such as the Non-Repeatable Run Out (NRRO). Vibrations and noise caused by the asynchronous components of the vibration frequency of the motor become large due to resonance phenomena occurring when a natural vibration frequency of the motor is the same or about the same as an excitation frequency occurring at the bearing when the motor rotates. Particularly, in hard disk drives, not only vibrations and noise are increased by resonance, but also NRRO is increased thereby causing servo track errors. Accordingly, spindle motors for hard disk drives are required to be free from the above-described resonance, and low in NRRO at rated rotations.

The excitation frequency of the bearing is a vibration frequency which occurs due to machining tolerance, warping, or the like, of the bearing components including the inner race, outer race, balls, and retainer. Resonance is generated in the event that the vibration frequency corresponds with the natural frequency of the motor.

In order to avoid the above-described resonance phenomena, the resonance phenomena was conventionally detected with the phenomena being visualized and indicated in accordance with the measured data such as vibrations and the like of the motor. As an example, FIG. 4 shows the vibration frequencies of a spindle motor visualized and indicated by a waterfall diagram. The waterfall diagram is a three-dimensional representation for indicating spectral waveforms of frequencies of vibration with the horizontal axis representing the frequencies, the vertical axis representing amplitude of vibration, and the depth-wise axis representing the number of rotations. The frequencies of vibration is obtained by steps of: measuring the vibrations generated by the spindle motor or the housing of the hard disk drive containing the spindle motor synchronously with change in rotations; subjecting the measured vibrations to amplification processing; and subjecting the frequencies of the measured vibrations to spectral analysis by using a FFT (fast Fourier transform) analyzer.

Presentation by the waterfall diagram visually indicates natural frequency characteristics of an object to be measured, e.g. a motor, such as at which frequency the vibration or amplitude peak of the measurement object is, the magnitude of vibration or amplitude peak values, how the vibration amplitude peak changes along with changes in rotations, and so forth.

On the other hand, in recent years, Campbell diagrams are coming into use for analysis of such resonance phenomena. As shown in FIG. 5, a Campbell diagram is a graph with the horizontal axis representing the motor rotations and the vertical axis representing the frequency, and can be considered to be a two-dimensional representation of the waterfall diagram shown in FIG. 4. In the Campbell diagram shown in FIG. 5, the amplitude of vibrations is represented by the diameter of the circles. Note that in FIG. 5, fr represents rotational frequency of the motor.

The waterfall diagram indicates change in vibrations according to rotational speed of a rotating apparatus, change in frequency components with time, change in natural frequencies due to temperature or the like. However, a Campbell diagram as shown in FIG. 5 is used to indicate such characteristics when it is required to identify the phenomena in a more precise manner.

However, when the conventional Campbell diagram indicates such vibration characteristics, the diagram includes graphic representation of all components of the measured data. Therefore, the excitation frequency of the bearing and components having far greater amplitude than the excitation frequency are indicated on the graph all together. In the present context, components considered to be "far greater" are those components which are significantly larger (e.g., as much as an order of magnitude, or more, larger), so as to overwhelm the remaining components. That is, it is difficult or impossible to discern a component when there is a far greater component at the same frequency. Accordingly, only the components with the very great amplitudes were visible, making it impossible to analyze and identify the vibration generating mechanism in order to identify the cause of abnormalities.

SUMMARY OF THE INVENTION

It is an object of the present invention to provide a characteristics indicating method which enables precise grasping of a phenomena from measured data, and also enables estimation of locations and modes of abnormalities.

The characteristics indicating method according to the present invention is for visually indicating vibration measurement data of a physical quantities or parameters such as displacement, speed, acceleration, sound pressure or the like from a measured object such as a rotating apparatus or vibrating apparatus, wherein specific components or parameters of the measurements are removed from the measurement data or minimized therein, and indicated in a Campbell diagram.

The characteristics indicating method of the present invention may be used to measure a rotating apparatus, including, for example, motors, turbines, or the like. The method of the present invention may also be used to measure a non-rotating vibrating apparatus, such as a smokestack, automobile, or the like. Slight asynchronous vibrations in the vibrations generated by the measured object while it is operating, can be visualized by removing or minimizing specific components or parameters having amplitudes far greater than those of the components to be indicated.

In an exemplary embodiment of the present invention for visualizing vibration, related measurement data generated by the measured object in operation having specific components with amplitudes far greater than those of the components to be indicated are removed or minimized. Such related measurement data may include, for example, data pertaining to the displacement, speed, acceleration, sound pressure, or the like, of the measured object. This enables a representation to be made on a Campbell diagram with amplitudes being represented by, for example, the size of circles centered on corresponding coordinates, one axis of which representing vibration frequencies and the other axis representing a physical quantity such as operating frequencies, time, temperature, or the like. In this way, the vibration state of the vibrating apparatus may be ascertained to more properly represent how the vibration varies with changes in operating frequencies, time, temperature, or the like.

In the event that the measured object is a motor having a rotor which is a principal moving part thereof and is rotatably supported by a stationary member via a ball bearing, indication is made by a Campbell diagram with one axis representing the vibration frequencies, the other representing rotor rotation. The size of figures such as circles centered on corresponding coordinates may be chosen to represent the amplitude. In accordance with this exemplary embodiment, the shapes are not necessarily circles but may be polygons such as triangles or quadrangles. Thus, the excitation source and resonance phenomena can be manifested in a more appropriately by the size of the figures. This provides an indication for grasping the resonance phenomena due to the correspondence of the bearing excitation frequency with the natural frequency.

One exemplary embodiment of the present invention involves removing or minimizing specific components of the measurement data having amplitudes far greater than those of the components to be indicated, indicating the measured data on a Campbell diagram, and superimposing excitation frequencies capable of generating vibration components at the bearing. This enables the identification of the excitation source. Also, if enlarged indication is made by amplifying the vibration frequency at the time of making the Campbell diagram indication, confirmation of the resonance phenomena can be easily made. Moreover, the types of lines and/or color or the like may be changed in accordance with the direction of vibration, vibration characteristics, or the like, for indication on figures such as circles. This allows identification of excitation frequencies of the bearing, or the like, to be indicated effectively, and identification of the characteristics of vibrations.

DETAILED DESCRIPTION OF THE PREFERRED EMBODIMENTS

An embodiment of the present invention will be described with reference to the drawings. In this embodiment, vibration measurement data are taken from a spindle motor of a hard disk drive. The spindle motor has a rotor which holds the hard disk and is rotatably supported by a stationary member via a ball bearing, and the excitation frequencies of the bearing are contained in the vibration frequencies of the motor.

Figure 1:
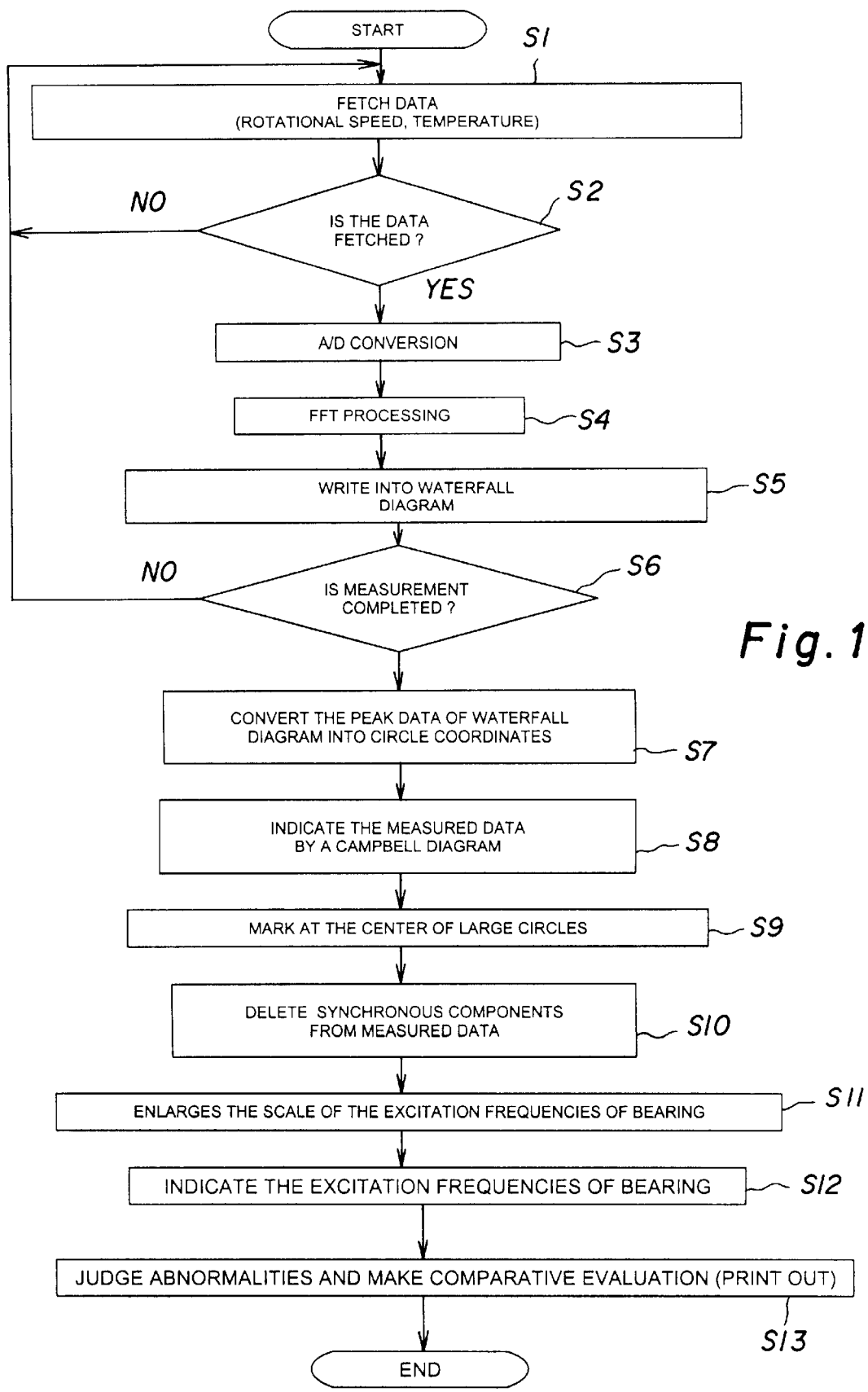
FIG. 1 is a flowchart illustrating an embodiment of the vibration characteristics indicating method according to the present invention.

FIG. 1 is a flowchart showing a process of the method of indicating characteristics, in accordance with the present invention. In the flowchart, S1 through S13 represent steps of the process.

Figure 4:
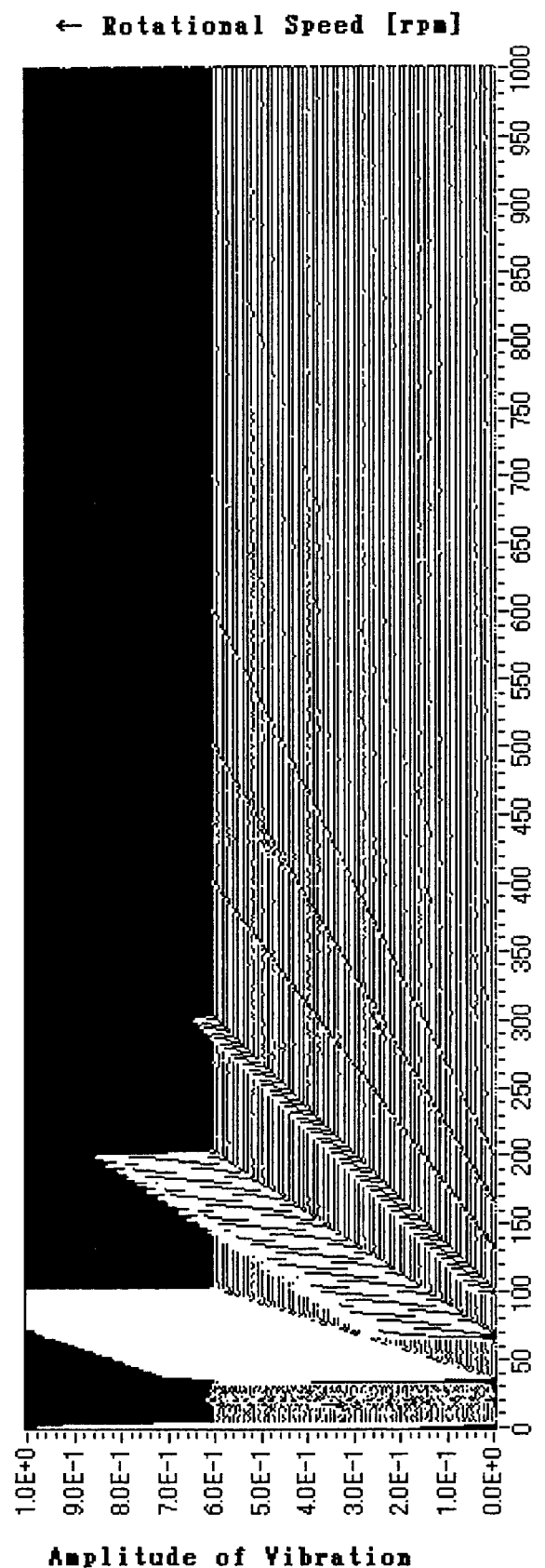
FIG. 4 is an example of a waterfall diagram.

Vibration of the rotor of the spindle motor is measured by a sensor which is in contact with, or in close proximity to, the spindle motor or the housing of the hard disk drive accommodating the spindle motor. The measured data of the vibration are taken in the circuit (S1 and S2). The data taken in is subjected to analog/digital conversion (S3). The converted data is analyzed in terms of frequency spectral by an FFT analyzer (S4). A waterfall diagram, as described in FIG. 4, is drawn with the analog data (S5). This data input process is repeated until measurement is completed (S6).

Once a series of operation is completed, including the steps of taking-in, converting, processing, and writing the measured data (when YES holds for the judgement at step S6), the peak value of the data written in the waterfall diagram is converted into circle coordinates. The respective circles have diameters corresponding to the peak values (S7) to show the characteristics by a Campbell diagram such as described in FIG. 5 (S8).

Figure 2:
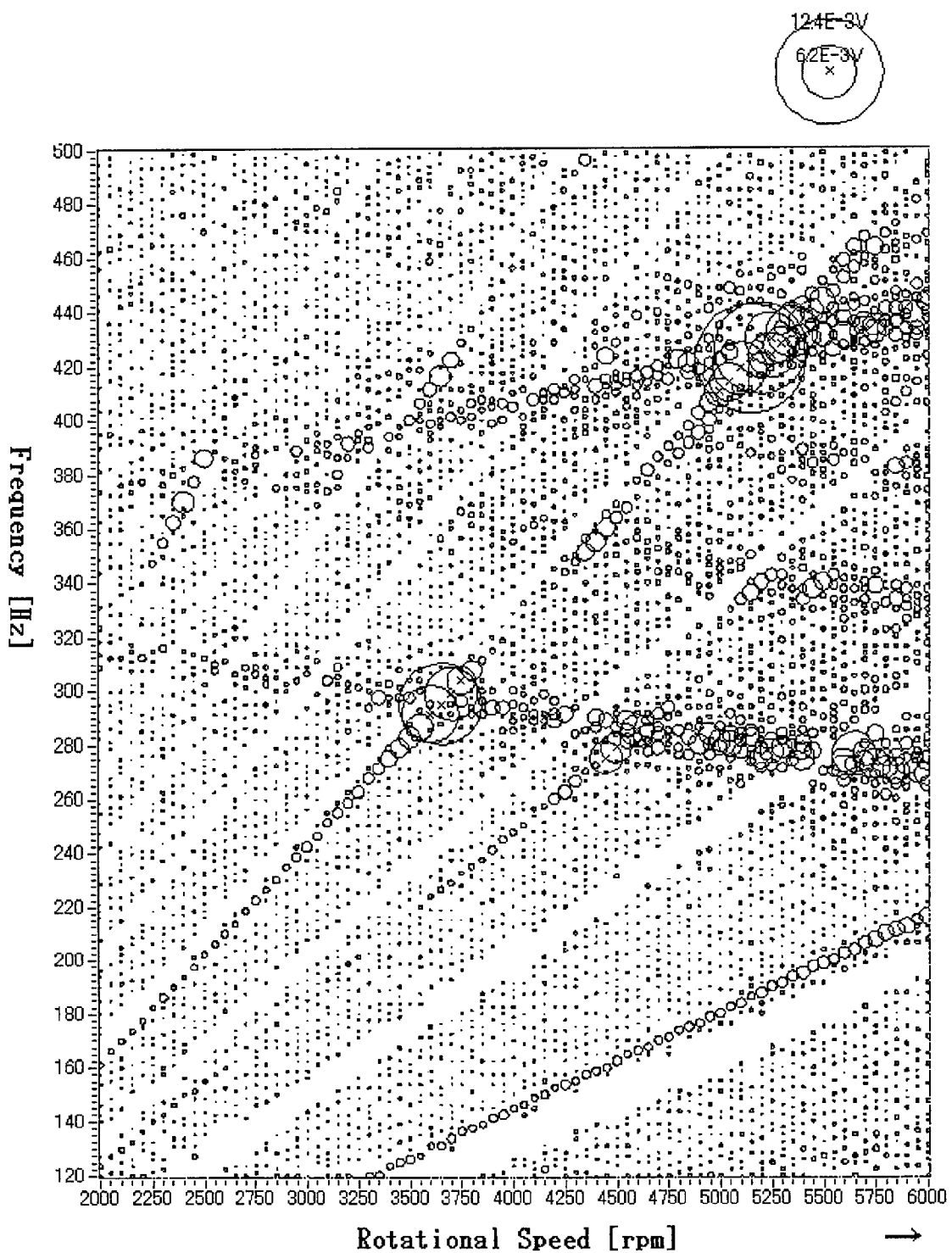
FIG. 2 is a characteristics diagram wherein measured data are indicated by a Campbell diagram after rotational synchronous components are removed from the measurement data according to the method shown in FIG. 1.
Figure 5:
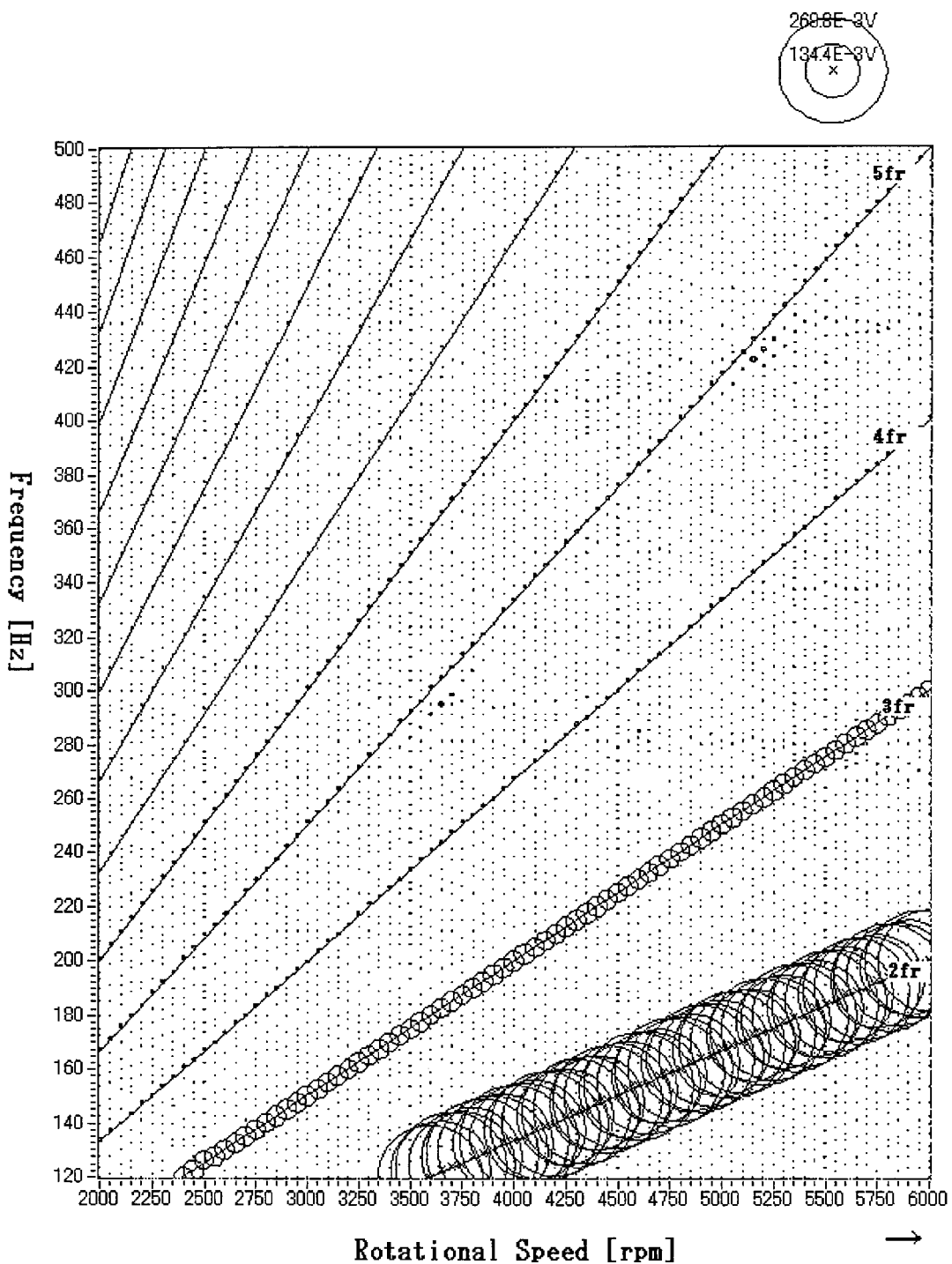
FIG. 5 is a characteristics diagram of measured data indicated by a Campbell diagram according to a conventional method.

In accordance with the present invention, the following steps S9 through S12 are performed in addition to a conventional method for indicating characteristics. In the Campbell diagram obtained at step S8, which appears as shown in FIG. 5, a mark (such as an X) is placed at each center of the large circles (S9). Then, the components synchronous with the rotation of the motor and having very great amplitude may be deleted from the measured data (S10). As such, the amplitude of vibration, i.e. the values of the measured data from which the synchronous component was removed, may be indicated on an enlarged scale by the Campbell diagram (S11). FIG. 2 shows a Campbell diagram thus obtained, wherein the synchronous component in FIG. 5 has been removed and remaining data are shown on a scale enlarged by approximately 20 times. The large circles in FIG. 2 indicate the resonance phenomena.

Figure 3:
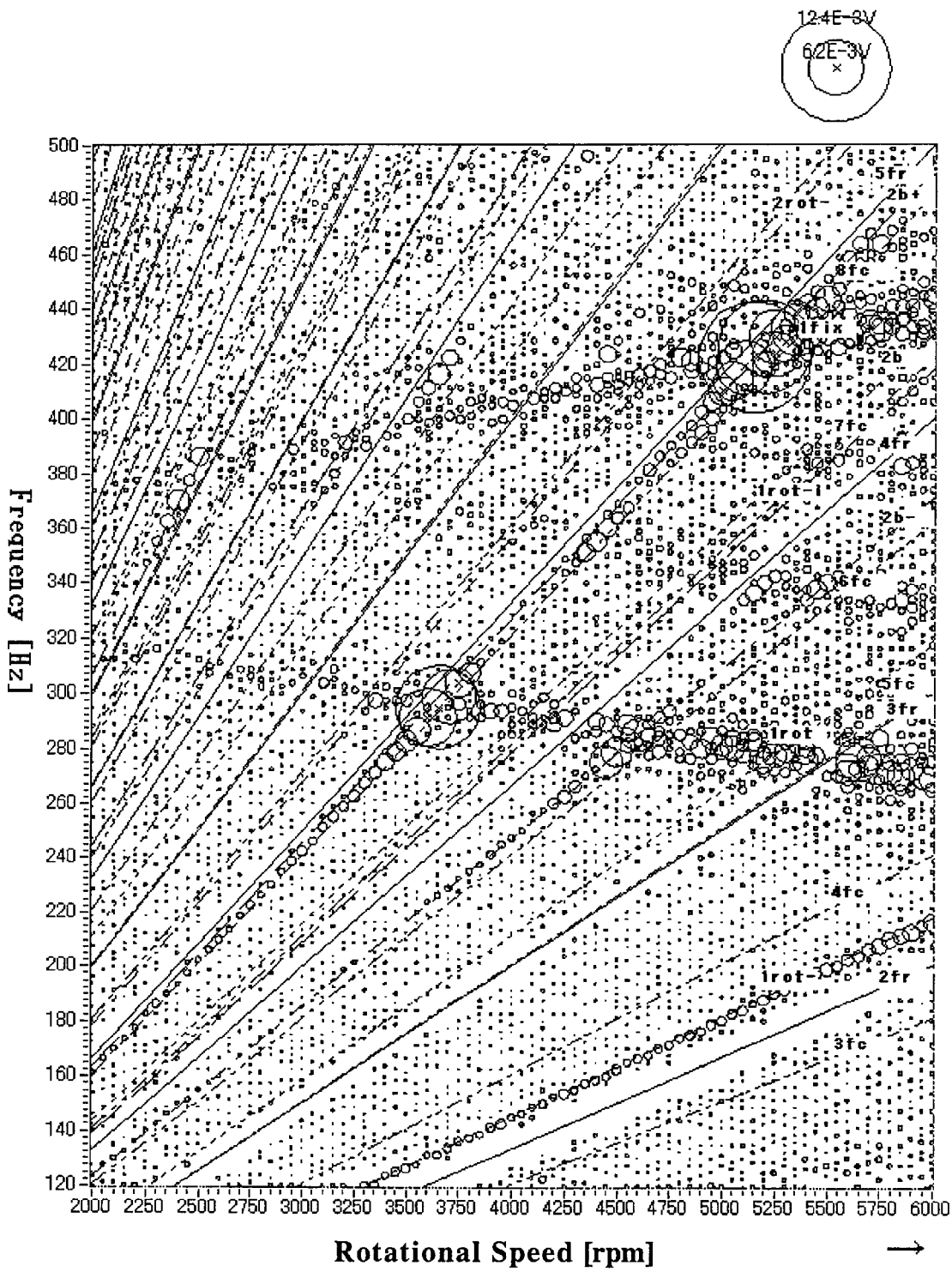
FIG. 3 is a Campbell diagram with excitation frequencies of the bearing being superimposed on a Campbell diagram shown in FIG. 2.

Further, the vibration frequency (excitation frequency) of the bearing, i.e., the NRRO generated by the bearing at each number of rotations, is additionally indicated on the Campbell diagram shown in FIG. 2 (S12) to obtain the Campbell diagram shown in FIG. 3. In the example shown in FIG. 3, the type of line is changed according to the directions of the bearing vibrations. As can be seen from FIG. 3, the excitation source can be identified from the mark at each center of the resonance portion circles and the lines and line types showing the bearing vibration frequency, whereby judgement and comparative evaluation of abnormalities may be performed, and the result of the judgement can be printed out as required (S13). In the example of FIG. 3, it is shown that the resonance phenomena occurring at the frequency of 290 Hz and at revolutions of 3600 rpm are due to the fixed race component (1fix) of the bearing, and that the resonance phenomena occurring at the frequency of 420 Hz and at revolutions of 5100 rpm are due to the secondary forward rotational component (2b+) of the ball.

Thus, a disadvantage of conventional Campbell diagrams is that all components or parameters in the graph are shown, so that only a synchronous component having very great amplitude in comparison to the bearing excitation component may be detected. In accordance with a method of the present invention, for example, the above-described embodiment, is that the state of vibration of the motor can be manifested wherein the component synchronous with rotation is deleted. In this way, an advantage of the present invention is that the remaining components may be shown on an enlarged scale. In addition, identification of the excitation source that causes vibration is facilitated by superimposing the excitation component of the bearing and the frequency thereof.

In accordance with one embodiment of the present invention, the vibration frequency of the bearing may be indicated with changing the types of lines. Alternatively, in accordance with the present invention the indication of circles or bearing excitation frequencies may be differentiated by changing the line type or the line color, according to the direction of vibration (radial, thrust, rotational direction, reverse-rotational direction, or the like), thereby facilitating the identification of the characteristic being indicated. Also, the horizontal axis may be chosen to represent the revolutions as in the embodiment mentioned above. Alternatively, the horizontal axis or other axis may be chosen to represent time, temperature, or a like variable, in order to grasp the change of NRRO with time, or the change of characteristic frequencies with temperature, using, for example, a Campbell diagram.

Also, in the above described example, vibration values are indicated in terms of change of sound pressure or, physical parameters relating to movement or fluctuation, e.g. amplitude, speed, acceleration, or jerk. The present invention is not limited to indication by such parameter may be applied to indications in terms of other physical parameters such as amount of warp or distortion, pressure fluctuation, force, electric current, voltage, light intensity, amount of light, magnetic flux, and so forth.

Also, though the above described embodiment deletes or cancels, the component of vibration frequency that is synchronous with rotation and has very great amplitude as compared to that of the bearing excitation component, and make the indication of remaining component on an enlarged scale, the objects of the present invention can be attained not only by deleting such specific components, but also minimizing them instead. That is to say, identification of excitation sources and estimation of the causes of abnormal operation can be made by applying a calculation or arithmetic operation to data having an amplitude greater than a certain level, e.g. such obstructive components as the rotation synchronous component or components of great amplitude to minimize the amplitude of the data to a level which does not affect the identification of the excitation source and the like.

Also, the application of the present invention is not limited to rotary device such as motors, but the invention may be applied to non-rotating vibrating device. For example, in order to see the state of vibration of a group of tubes placed within a fluid, a diagram may be made wherein the horizontal axis represents the speed of the fluid, the magnitude of vibrations is represented by pressure fluctuation within the tubes, and fluid excitation frequencies generated by Karman's vortex is superimposed as the excitation frequency.

The characteristics indicating method described in detail above deletes or minimizes particular components of data measured for an object such as a rotating apparatus or a vibrating apparatus and then indicates the measured and operated data on a Campbell diagram, thus visualizing extremely minute asynchronous vibrations and the like, and manifesting the vibration state.

Also, particular components of the data measured for an object under operation are deleted or minimized, and the remaining data is indicated for the Campbell diagram with one axis representing the operating frequency or time or temperature, or the like, and the magnitude of the vibration is indicated by a size of a circle of which center is at a specified coordinate on the diagram, thereby enabling manifestation of the state of the vibration. As described above, the figure may not necessarily be circle but may be other shapes. Thus, in more general, the center position of the figures such as a circle and the size of the figure visualize the state of vibration, and also indicate the vibration state in response to changes in operating frequencies, time, temperature, or the like.

Further, particular components of the data measured for a rotor which is supported via a ball bearing as the object to be measured are deleted or minimized, and Campbell diagram indication is made with the rotation and the frequencies of the motor being represented by two axes of a coordinates, and the magnitude of the vibration being indicated as the size of a circle centered at the corresponding coordinate, so the excitation source causing vibrations and the resonance can be precisely manifested by the size of the circles, thereby realizing an optimal indication for grasping resonance phenomenon due to correspondence between excitation frequencies of bearing and natural frequencies.

In addition, the excitation component of the bearing or the like is superimposed on the Campbell diagram which indicates the measured data after deletion or minimization of particular components, so the excitation sources causing the resonance phenomena can be identified on the Campbell diagram. With the characteristics indicating method according to one aspect of the present invention, the measured data after the deletion or minimization of particular components is indicated on a Campbell diagram and also the vibration amplitude is indicated on an enlarged scale, so visualization of the resonance phenomena is facilitated, and also the indication of circles or excitation frequencies of bearing may be differentiated by changing the type, color or the like of the lines according to the direction of vibration, so further identification of state of vibration, excitation source or the like is facilitated.

What is claimed is:

1. A method for indicating characteristics of rotating apparatus or vibrating apparatus, the method comprising steps of:

measuring data of vibration by a physical parameter of displacement, speed, accelerated velocity or sound pressure level of a measured object;

filtering or minimizing a specific element from the data of vibration to provide processed data;

removing or minimizing specific components from or within the data of vibration; and indicating the characteristics of the measured object by displaying the processed data as a Campbell diagram such that amplitudes are represented by size of circles, said circles being centered on corresponding coordinates with one axis representing vibration frequencies and an other axis representing a physical quantity of operating frequencies, time, or temperature.

2. A method for indicating characteristics according to claim 1, wherein;

said measured object is a motor including a rotor as a principal moving part thereof, wherein said rotor is rotatably supported by a stationary member thorough a bearing means;

the data of vibration is an amount of vibration of the motor measured by a sensor; and the Campbell diagram being made such that one axis represents vibration frequencies, an other represents rotor rotation, and shapes centered on corresponding coordinates represent amplitude.

3. A method for indicating characteristics according to claim 2, wherein excitation frequencies of the bearing means are superimposed on the processed data displayed by the Campbell diagram, with the specific components being removed or minimized.

4. A method for indicating characteristics according to claim 3, wherein the circles or the excitation frequencies of the bearing are differentiated by changing a line type color of lines of said circles according to a direction of vibration.

5. A method for indicating characteristics according to claim 1, wherein a vibration amplitude is indicated on an enlarged scale on the Campbell diagram, with the specific components being removed or minimized.

* * * * *